US012766016B2

(12) United States Patent
Walsh et al.

(10) Patent No.: US 12,766,016 B2
(45) Date of Patent: Oct. 20, 2026

(54) LUMEN APPOSING STENT TO DELIVER TARGETED THERAPY

(71) Applicant: BOSTON SCIENTIFIC SCIMED, INC., Maple Grove, MN (US)

(72) Inventors: Kevin Walsh, Wellesly, MA (US); Sean P Fleury, Princeton, MA (US); David Callaghan, Ashland, MA (US); Laura Emily Richards, Worcester, MA (US); John Thomas Favreau, Spencer, MA (US); James J Scutti, Norwell, MA (US)

(73) Assignee: Bosto Scientific Scimed, Inc., Maple Grove, MN (US)

( * ) Notice: Subject to any disclaimer, the term of this patent is extended or adjusted under 35 U.S.C. 154(b) by 911 days.

(21) Appl. No.: 17/747,406

(22) Filed: May 18, 2022

(65) Prior Publication Data

US 2022/0370219 A1 Nov. 24, 2022

Related U.S. Application Data

(60) Provisional application No. 63/190,491, filed on May 19, 2021.

(51) Int. Cl.
*A61F 2/966* (2013.01)
*A61F 2/07* (2013.01)
(Continued)

(52) U.S. Cl.
CPC ................ *A61F 2/915* (2013.01); *A61F 2/07* (2013.01); *A61F 2/88* (2013.01); *A61F 2250/0067* (2013.01)

(58) Field of Classification Search
CPC .. A61F 2/962; A61F 2250/0068; A61F 2/064; A61F 2/06; A61F 2230/0095;
(Continued)

(56) References Cited

U.S. PATENT DOCUMENTS

| | | | |
|---|---|---|---|
| 6,053,900 | A | 4/2000 | Brown et al. |
| 2004/0010309 | A1 | 1/2004 | Seward et al. |

(Continued)

FOREIGN PATENT DOCUMENTS

| | | | |
|---|---|---|---|
| CN | 106420129 B | 2/2019 |
| EP | 2526904 A1 | 11/2012 |

(Continued)

OTHER PUBLICATIONS

Translation of KR 20140051338 (Year: 2014).*

(Continued)

*Primary Examiner* — Brian E Pellegrino
(74) *Attorney, Agent, or Firm* — Seager, Tufte & Wickhem, LLP

(57) ABSTRACT

Devices, systems, and methods for delivering targeted therapy to tissue at a treatment site with the use of a stent. The targeted therapy may include a functional and/or therapeutic agent separate from the stent, or a component of a functional and/or therapeutic agent separate from the stent and reactive with another component of a functional and/or therapeutic agent on the stent. The agent or component of an agent may be delivered with the stent, and/or before delivery of the stent, and/or after the stent has been delivered.

20 Claims, 10 Drawing Sheets

(51) Int. Cl.
*A61F 2/88* (2006.01)
*A61F 2/915* (2013.01)

(58) Field of Classification Search
CPC .... A61F 2/82; A61F 2/966; A61F 2250/0067; A61F 2210/0076; A61M 2025/0057; A61M 2025/0056; A61M 2025/0062
USPC .......................................................... 606/192
See application file for complete search history.

(56) References Cited

U.S. PATENT DOCUMENTS

| | | | |
|---|---|---|---|
| 2004/0143315 | A1 | 7/2004 | Bruun et al. |
| 2006/0058866 | A1 | 3/2006 | Cully et al. |
| 2006/0184237 | A1 | 8/2006 | Weber et al. |
| 2006/0265043 | A1 | 11/2006 | Mandrusov et al. |
| 2016/0082248 | A1 | 3/2016 | Shuros et al. |
| 2017/0340434 | A1 | 11/2017 | Cerchiari et al. |
| 2018/0250501 | A1 | 9/2018 | Hingston et al. |

FOREIGN PATENT DOCUMENTS

| | | | | | |
|---|---|---|---|---|---|
| EP | 2821467 | A1 * | 1/2015 | ............. | A61L 29/14 |
| JP | 2006515786 | A | 6/2006 | | |
| KR | 20140051338 | A * | 4/2014 | ........... | A61F 2/9522 |
| WO | WO-9632078 | A1 * | 10/1996 | ............. | A61F 2/966 |
| WO | 9940853 | A1 | 8/1999 | | |
| WO | WO-2011050979 | A1 * | 5/2011 | ............... | A61F 2/07 |
| WO | 2018181326 | | 10/2018 | | |

OTHER PUBLICATIONS

International Search Report and Written Opinion dated Sep. 6, 2022 for International Application No. PCT/US2022/029800.

Rao et al; "Peptide Growth Factors In GI Mucosal Growth", pp. 1-6, San Rafael, CA: Morgan and Claypool Life Sciences: 2010, Accessed Mar. 22, 2021.

* cited by examiner

LUMEN APPOSING STENT TO DELIVER TARGETED THERAPY

CROSS-REFERENCE TO RELATED APPLICATIONS

This application claims the benefit of priority of U.S. Provisional Application No. 63/190,491, filed May 19, 2021 disclosure of which is hereby incorporated by reference herein for all purposes.

FIELD

The present disclosure relates generally to the field of medical devices, systems, and methods for operatively delivering a functional and/or therapeutic agent to a body, such as to body tissue. More particularly, the present disclosure relates to medical devices, systems, and methods utilizing a device as a scaffold on which a functional and/or therapeutic agent may be deposited and delivered to a body, such as in situ.

BACKGROUND

Various implantable devices are used for a number of treatment protocols and procedures. For instance, stents, such as self-expanding metal stents (SEMS), may be used within an anatomical area (e.g., body lumen, passage, vessel, duct, etc.) to enable fluid communication from one area to another, such as through a body lumen, or from one anatomical structure (e.g., body lumen or cavity or organ) to another anatomical structure (e.g., body lumen or cavity or organ). Stents, such as lumen apposing stents, may be used to increase and improve access to different anatomical regions, such as within the gastrointestinal (GI) tract. Current uses of lumen apposing stents include drainage of pancreatic pseudocysts and antegrade access to the gallbladder. Stents may also be used to hold body tissues in apposition. One challenged faced when using stents is that various forces (e.g., as a result of the patient's natural motion or involuntary movements within the body, such as peristaltic movements along the GI tract) may increase a risk for migration of the stent. Migration of an implanted stent may result in fluid leakage, discomfort for the patient, and/or an additional procedure to replace the stent. Different devices, systems, and methods for reducing or preventing migration of a deployed stent thus would be welcome in the industry. Moreover, expansion of uses of stents, such as for closure of full thickness resections, by addressing various challenges presented by such procedures, would also be welcome in the industry. Finally, different secure and efficient mechanisms for applying agents or substances to the target/deployment site of the stent during or after deployment would be welcome in the industry as well.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with an aspect of the present disclosure, a system for maintaining a flow path in tissue is provided with a first sheath, a stent disposed within the first sheath, and a second sheath disposed about the first sheath. In some embodiments, the stent is configured to transition between a first configuration and a second configuration. In some embodiments, a functional and/or therapeutic agent is disposed between the first sheath and the second sheath.

In some embodiments, the functional and/or therapeutic agent includes an agent selected from the group including of: an adhesive agent, a healing agent, a therapeutic agent.

In some embodiments, the stent is disposed about an inner member; and the first sheath is proximally longitudinally retractable with respect to the inner member, the inner member is distally longitudinally extendable with respect to the first sheath, or both, such that the stent is released from within the first sheath to transition to the second configuration.

In some embodiments, the first functional and/or therapeutic agent component is disposed between the first sheath and the second sheath, and the second functional and/or therapeutic agent component is disposed over the stent when disposed within the first sheath.

In accordance with another aspect of the present disclosure, a system is disclosed as having a stent including a lumen extending longitudinally therethrough, the stent configured to shift between a first configuration and a second configuration; and a functional and/or therapeutic agent. In some embodiments, in the second configuration, the stent defines a first retention member, a second retention member, and a saddle region extending therebetween, and when the stent is positioned within a body lumen in the second configuration, the first retention member, the second retention member, the saddle region, and the tissue wall of the lumen define a volume configured to retain the functional and/or therapeutic agent therein.

In some embodiments, the first retention member and the second retention member are configured to space the tissue away from the saddle region.

In some embodiments, the functional and/or therapeutic agent includes an agent selected from the group including of: an adhesive agent, a healing agent, a functional or therapeutic agent.

In some embodiments, the system further includes a fluid delivery device configured to inject the functional and/or therapeutic agent. In some embodiments, the fluid delivery device is configured to inject the functional and/or therapeutic agent through the tissue wall and into the volume defined by the stent and the tissue wall. In some embodiments, the fluid delivery device is configured to extend through one of the first retention member or the second retention member to inject the functional and/or therapeutic agent into the volume defined by the stent and the tissue wall.

In some embodiments, the stent further includes another functional and/or therapeutic agent disposed therealong.

In accordance with another aspect of the present disclosure, a method for creating an anastomosis includes advancing a delivery system from a first lumen across first and second tissues and into a second lumen. In some embodiments, the delivery system includes a first sheath, an inner member, a stent disposed within the first sheath and about the inner member, a second sheath disposed about the first sheath, and a functional and/or therapeutic agent disposed between the first sheath and the second sheath. In some embodiments, the stent is configured to transition between a first configuration and a second configuration. In some embodiments, the method also includes proximally retracting the first and second sheath with respect to the inner member, distally extending the inner member with respect to the first sheath and second sheath, or both, such that a first end of the stent is extended distally outside the first sheath and forms the first retention member within the second body lumen, and the functional and/or therapeutic agent is disposed on a surface of the stent. In some embodiments, the method further includes proximally retracting the first sheath with respect to the inner member, distally extending the inner member with respect to the first sheath, or both, such that a second end of the stent is unconstrained from the first sheath and forms the second retention member within the first body lumen.

In some embodiments, the method further includes disposing the functional and/or therapeutic agent on the surface of the saddle region of the stent upon proximally retracting the first sheath with respect to the inner member, distally extending the inner member with respect to the first sheath, or both.

In some embodiments, the method further includes disposing the functional and/or therapeutic agent on the surface of the second retention member upon proximally retracting the first sheath with respect to the inner member, distally extending the inner member with respect to the first sheath, or both.

In some embodiments, the method further includes disposing an additional functional and/or therapeutic agent along a surface of the saddle region.

In some embodiments, disposing the additional functional and/or therapeutic agent includes injecting the additional functional and/or therapeutic agent via a needle.

In some embodiments, the inner member includes a cutting element disposed at an end thereof, and the method further includes forming an anastomosis across the first and second tissue with the cutting element before extending the first end of the stent distally outside the first sheath.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component in each embodiment of the disclosure shown where illustration is not necessary to allow those of skill in the art to understand the disclosure. In the figures.

DETAILED DESCRIPTION

Figure 1A:
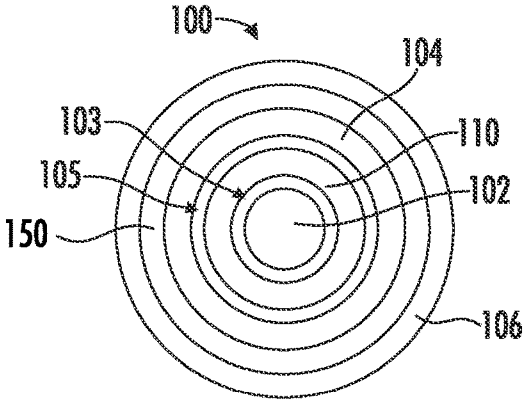
FIGS. 1A-1B illustrate end and side views of a system for deploying a stent with a functional and/or therapeutic agent according to one or more embodiments described herein.

The following detailed description should be read with reference to the drawings, which depict illustrative embodiments. The present disclosure is not limited to the particular embodiments described, as such embodiments may vary. The terminology used herein is for the purpose of describing particular embodiments only and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory system, and the like. The structures and configurations, and methods of deploying, in order to stabilize, maintain, and/or otherwise facilitate fluid flow paths may find utility beyond treatments discussed herein.

As used herein, "proximal end" refers to the end of a device that lies closest to the user (medical professional or clinician or technician or operator or physician, etc., such terms being used interchangeably herein without intent to limit, and including automated controller systems or otherwise) along the device when introducing the device into a patient, and "distal end" refers to the end of a device or object that lies furthest from the user along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges or values by endpoints includes all numbers within that range, including the endpoints (e.g. 1 to 5 includes 1, 1.5, 2, 2.75, 3, 3.80, 4, and 5), and fractions thereof.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

It is noted that the specification and figures may refer to examples of stents. It is presently contemplated that methods and features described herein are applied to stents as understood in a broad sense and apply to a variety of devices such as grafts, tissue scaffolds, other medical implants or self-expanding or expandable structures, etc. Reference to stents herein will be understood to include reference to such appropriate devices implicitly for the sake of brevity and without intent to limit.

Various procedures involve the creation and/or maintenance of a flow path through at least one body lumen and/or across tissues, for example, for the flow and/or drainage of fluid therethrough. A medical device such as a stent, graft, or the like may be used to hold open the flow path. In many procedures, a stent, graft, or other medical device for maintaining an open flow path may be implanted endoscopically. Various additional or alternative procedures involve use of a stent, graft, or other medical device to hold together portions of a body tissue (such as to heal a lesion) or to hold together apposed body tissues. Such procedures may be advantageously performed endoscopically, as endoscopic procedures can be less invasive than traditional open or lap surgery procedures. For example, an endoscope may be introduced into a body lumen without the need for extensive surgical incisions.

Various challenges have heretofore been encountered with such procedures. Natural motions of a patient may result in various forces being applied to an implanted medical device, which may increase a risk of the medical device to migrate. Additionally, or alternatively, the implantation of a medical device into a body may elicit an immune response from surrounding tissue. Any of these risks may result in undesirable irritation of tissue and/or discomfort for a patient. In the event of device migration, fluids may leak undesirably around the device, for example, into other areas of the body, which may contribute to further discomfort and/or risk for the patient. Subsequent procedures may be necessary to reposition or retrieve a dislodged or migrated medical device.

Accordingly, there is a need for improved systems to maintain a position of implanted medical devices and/or to prevent, reduce, or otherwise manage irritation of tissue surrounding the implants. More generally, there is a need for increased functionality of implanted devices, such as to permit application of a wider variety of functional and/or therapeutic agents to a deployment site of the device. It will be appreciated that terms such as application, deployment, delivery, provision, etc. (and conjugations and other grammatical forms thereof) of a functional and/or therapeutic agent may be used interchangeably herein without intent to limit unless otherwise indicated.

With the above considerations in mind, a variety of advantageous medical outcomes may be realized by the devices and/or methods of the present disclosure below.

For example, a stent may be deployed in or across body tissues or lumens with at least one functional and/or therapeutic agent selected for treating the tissue at the deployment site. In some embodiments, the agent provides a mechanical effect, such as aiding in or promoting adherence of the tissue to other tissue (e.g., to close a lesion or to form an anastomosis or otherwise to hold together apposed tissues) or to the stent (such as to hold the stent in place with respect to the deployment site to resist migration). In some embodiments, the agent provides a biological cellular therapeutic effect, such as hemostasis, facilitating healing, aiding in management of irritation and/or inflammation of the surrounding tissue, reducing discomfort, and/or reducing infection (e.g., such as including an antibacterial agent). Examples of agents with adhesive properties which may be used with devices, systems, and methods of the present disclosure include, without limitation, cyanoacrylate, LED cured adhesive, hydrogel, etc. Examples of agents with healing properties (e.g., tissue healing agents) include, without limitation, silk hydrogel, chitin hydrogel, growth factor gels, anti-inflammatory agents, antibacterial and other anti-microbial agents (including, without limitation, agents including biocidal and biostatic properties), antibiotic agents, hemostatic agents, sclerosing agents, discomfort-reducing agents (including, without limitation, antispasmodic agents, ketorolac, corticosteroids, narcotic analgesic agents, non-narcotic analgesic agents, local anesthetic agents, alpha-adrenergic blockers, and combinations thereof), anti-growth agents, growth-promoting agents, etc. Examples of agents with therapeutic and/or protective properties include, without limitation, chemotherapy agents, bioabsorbable gels as carriers for imaging and/or therapy agents, growth factors inhibitors, anti-cancer drugs (e.g., including agents such as alkylating agents, antimetabolites, antimitotics, hormones, immunosuppressives, etc.), etc. The functional and/or therapeutic agent may be provided in any desired form suitable for the intended purpose, such as a suspension, bound to a polymer, compounded into a coating, etc. Any appropriate delivery agent or carrier, such as a hydrogel, (e.g., Polyvinyl Alcohol (PVA), Sodium Alginate (SA), Carboxy Methylcellulose (CMC), Hyaluronic Acid (HA), Hydroxypropyl Methyl Cellulose, Hydroxyethyl Starch (HES), Xanthan Gum (XG), Gellan Gum, Gelatin, Agar, Polylactic Acid (PLA), Chitosan, Lecithin) may be used for such agents. The functional and/or therapeutic agent may be in any desired weight per volume of delivery agent or carrier as indicated to achieve the desired functional and/or therapeutic effect. For instance, the functional and/or therapeutic agent may be suspended or compounded in the delivery agent or carrier at a desired weight per volume of delivery agent or carrier. The injection force of the agent/gel, excluding the force of stent deployment, preferably is less than 60N. The viscosity at a desired shear rate preferably does not result in injection forces of over the clinically acceptable level for the procedure and should be less than 60N. Moreover, the delivery agent or carrier may be formulated to react to the environment in which it is placed, such as by absorbing water and swelling, or by releasing water and shrinking, or by otherwise affecting release of the functional and/or therapeutic agent therefrom. It will be appreciated that the above-listed agents may be any known or heretofore known agent in the art, the broad principles of the present disclosure not being limited by particular examples. Embodiments are not limited in this context. Methods and systems described herein may accommodate deployment of stents and one or more functional and/or therapeutic agents together or in separate steps. Percutaneous and intraductal deployment methods are presently contemplated.

The present disclosure provides devices, systems, and methods for providing a functional and/or therapeutic agent in association with a device or structure such as a stent. For the sake of convenience, reference is made to a stent without intent to limit, such reference being intended to encompass other devices and/or structures suitable for use in accordance with various principles of the present disclosure, such as any structure which may form or provide a scaffold for a functional and/or therapeutic agent to be applied thereto and to be maintained thereon for delivery and/or application to tissue at a treatment site.

Agents such as adhesive agents, healing agents, and/or therapeutic/protective agents may be delivered with or to the stent in accordance with various principles of the present disclosure. The functional and/or therapeutic agent may be applied to the surface of the stent as it is deployed. Additionally or alternatively, the stent may carry or be provided with (such terms, and other similar terms, being used interchangeably herein without intent to limit) a component of a functional and/or therapeutic agent, which may be inactive until activated, such as at the deployment site. Another component of a functional and/or therapeutic agent may be applied to the surface of such stent upon deployment of the stent so that the components of the agent may interact or be activated in situ at the deployment site (or shortly before deployment, such as during the deployment procedure, such as during delivery of the stent). Additionally or alternatively, the stent may be configured to accept or to receive a functional and/or therapeutic agent after the stent has been deployed, and preferably to retain such agent with respect to tissue along which the stent is deployed to achieve the desired functional and/or therapeutic effect with respect to the tissue. In some embodiments, a gel as a carrier for an active agent may be formed in situ. For instance, one component could be a polymer for a gel, and the other component could be a cross-linking agent that instantly forms a gel when the two components are combined, or the gel could be thermosensitive and form a gel when exposed to body temperature (e.g., tissue at body temperature).

One particular benefit of various principles of the present disclosure is the ability to deliver a functional and/or therapeutic agent that is not activated until deployment. For instance, various conditions at the deployment site (e.g., contact with body tissue at the deployment site, contact with material of the stent, exposure to body fluids at the deployment site, exposure to body temperature, etc.) may trigger activation of the functional and/or therapeutic agent, which may be delivered in an inactivated state. Another benefit is the ability to customize a given stent for the therapeutic needs of the patient by selecting one or more of a variety agents to be used in conjunction with a stent not otherwise initially bearing or carrying or otherwise being associated with a particular agent, thereby expanding potential uses of a given stent.

In accordance with various principles of the present disclosure, a stent is configured to provide a region for retaining a functional and/or therapeutic agent against or adjacent tissue to be treated. For instance, the stent may have a longitudinal extent when in a deployed configuration defining a first retention member along a first end, a second retention member along a second end, and an intermediate region between the first and second retention members. The first retention member has a first diameter, the second retention member has a second diameter, and the intermediate region has an intermediate diameter less than both the first diameter and the second diameter. As such, a functional and/or therapeutic agent may be retained or contained between the first and second retention members and along the intermediate region. For instance, a functional and/or therapeutic agent may be provided or deployed or deposited (such terms, and similar other terms, begin used interchangeably herein without intent to limit), and retained within a volume extending about the intermediate region, between the retention members, and between the stent and tissue along which the stent is positioned, to provide a desired effect with respect to the tissue.

The various principles of the present disclosure may be applied to any of a variety of configurations of stents. For instance, principles of the present disclosure may be applied to stents configured for draining an anatomical region, or for opening or creating or maintaining or treating a flow path, or for holding together apposed tissue (such as to close a wound or lesion or to form an anastomosis), or for other therapeutic purposes. In some embodiments, the stent may simply provide a structure or scaffold for the functional and/or therapeutic agent. Principles of the present disclosure may be applied to expand or improve or enhance usage of stents in conjunction with full thickness resections of tissue, such as by using the stent to effect closure of the resected tissue.

A delivery and deployment system for delivering and deploying a stent and accompanying functional and/or therapeutic agent may include a handle with a first control knob for a first sheath positioned over the stent, a second control knob for a second sheath positioned over the first sheath, and a third control knob for an inner member on which the stent is deployed, each control knob capable of independent movement of the other control knob. A first port may be provided to access a guide lumen or channel through the inner member, such as for delivery of guidewire (e.g., to assist in navigating to the desired deployment site) or needle or injectable material (e.g., imaging materials a fluoroscopy agent such as a contrast agent). A second port may be provided to deliver a functional and/or therapeutic agent to the stent, including, without limitation, to the deployment site before the stent is delivered, over the stent as it is being deployed, over an already-deployed stent, and/or adjacent an already deployed stent.

The detailed description should be read with reference to the drawings, which are not necessarily to scale, which depict illustrative embodiments and are not intended to limit the scope of the invention.

Figure 1B:
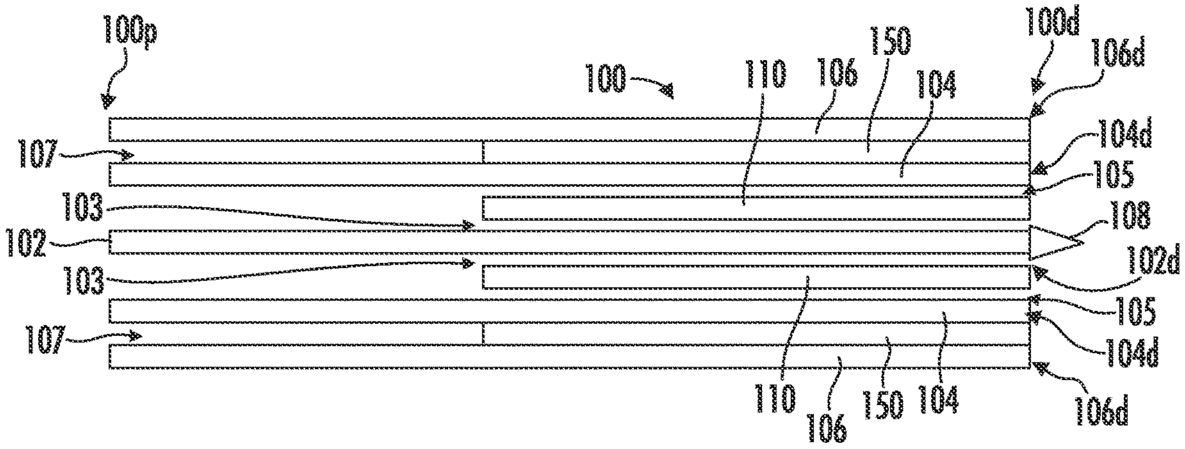

Turning now to the drawings, as illustrated in FIGS. 1A-1B, various systems according to the present disclosure, including deployment system 100, may include a stent 110 positioned between an inner member 102 and a first sheath 104 of the deployment system 100. Stent 110 may be configured to shift between a first configuration (e.g., collapsed configuration, constrained configuration, elongate configuration, delivery configuration, or the like) and a second configuration (e.g., expanded configuration, unconstrained configuration, deployed configuration, or the like). For the sake of simplicity and without intent to limit, a first configuration as described herein will be understood to additionally or alternatively refer to a constrained configuration, elongate configuration, delivery configuration, or the like, and a second configuration as described herein will be understood to additionally or alternatively refer to an unconstrained configuration, expanded configuration, deployed configuration, or the like. Stent 110 is illustrated in FIGS. 1A-1B in a first configuration but may have a second configuration with one or more similarities to the second configuration of stent 210 as illustrated in FIGS. 2B-2D.

Stent 110 may be solid, woven, knit, or other recognizable form of stent, and may be made of metal, polymer, silicone, or other material. In various embodiments, stent 110 may be formed of a shape memory material. For example, stent 110 may be formed of one or more shape memory wires, such as Nitinol, Platinol, and the like alloys. Stent 110 may be preset to a second configuration and subsequently constrained within first sheath 104. Various known or heretofore known covers (not illustrated for the sake of simplicity in the drawings), such as polymeric or elastomeric or silicone or lubricious coatings, may be applied to selected regions of the stent 110. It will be appreciated that terms such as covers, coatings, sheaths, etc., may be used interchangeably herein without intent to limit terms. Provision of a cover may contribute to the mechanics of stent 110, impart structural stability, occlude (partially or fully) flow of materials through the walls of the stent 110, and/or inhibit tissue ingrowth. Selected regions of the stent 110 may be remain uncoated to permit tissue ingrowth to resist migration of the stent 110, with optionally-coated regions resisting collapse and migration, thus facilitating sufficient immobility to allow for ingrowth into the uncoated regions.

Stent 110 may be disposed between first sheath 104 and inner member 102 such that stent 110 is held within the first configuration. A first intervening space 103 and/or a second intervening space 105 may exist between stent 110 and the respective inner member 102 or first sheath 104. It will be appreciated that first intervening space 103 and/or second intervening space 105 are optional and may not be large enough to enable stent 110 to loosely rest within first sheath 104. In various embodiments, inner member 102 and first sheath 104 may hold stent 110 securely therebetween.

A second sheath 106 may be disposed about first sheath 104. A functional and/or therapeutic agent 150 may be disposed in a space 107 between first sheath 104 and second sheath 106. Functional and/or therapeutic agent 150 may be in the form of a solid sheath, a semi-solid sheath, or a fluid (e.g., gel or liquid). In any event, but particularly in examples in which functional and/or therapeutic agent 150 comprises a fluid, a cap 180 as illustrated in FIG. 8 (and described in further detail below) may be provided along distal end 100*d* of deployment system 100 such as by being fitted to distal end 104*d* of at least first sheath 104 and/or distal end 106*d* of second sheath 106 prior to a procedure and/or until a practitioner is ready to release functional and/or therapeutic agent 150. Alternatively or additionally, a membrane may be provided along distal end 100*d* of deployment system 100, the membrane being thin enough or otherwise configured to be puncturable by a stylet passed through space 107, breached by pressure of an agent, or dissolvable (e.g., at body temperature).

In various embodiments, functional and/or therapeutic agent 150 may comprise adhesive and/or healing and/or other treatment (e.g., tissue treatment) properties. For example, functional and/or therapeutic agent 150 may comprise one or more of the following: a glue or sealant or other agent with adhesive properties (e.g., cyanoacrylate, LED cured adhesive, hydrogel, etc); various healing hydrogels/gels (e.g., silk hydrogel, chitin hydrogel, growth factor gels) and/or other healing agents (anti-inflammatory agents); growth factors and/or inhibitors; therapeutic and/or protective agents (e.g., chemotherapy and/or radiation therapy agents); or the like, such as described above. Embodiments are not limited in this context.

In some embodiments, a cutting element 108 may be positioned at or on a distal end 102*d* of inner member 102. For example, cutting element 108 may comprise an electrocautery tip, a blade or sharpened needle tip, or the like, which may be configured to puncture or cut through tissue. The cutting element 108 may be used to create a pathway through tissue through which the stent 110 may be extended. In some embodiments, a lumen or channel is formed through inner member 102 through which a guidewire may be passed and used to guide the stent 110, inner member 102, first sheath 104, and second sheath 106 to the deployment site. Additionally or alternatively, such lumen or channel may be used to deliver a needle, an injectable, etc., therethrough.

In various embodiments, one or both of first sheath 104 and second sheath 106 may be distally longitudinally extendable (towards distal end 100*d* of deployment system 100) and/or proximally longitudinally retractable (towards proximal end 100*p* of deployment system 100) with respect to inner member 102 and/or to each other. Inner member 102 may be distally longitudinally extendable and/or proximally longitudinally retractable with respect to first sheath 104 and/or second sheath 106. In various embodiments, distal longitudinal extension of inner member 102 with respect to first sheath 104 and/or proximal longitudinal retraction of first sheath 104 with respect to inner member 102 may allow stent 110 to transition from its first configuration (when within first sheath 104) to its second configuration upon exiting or being unsheathed from first sheath 104.

Figure 7:
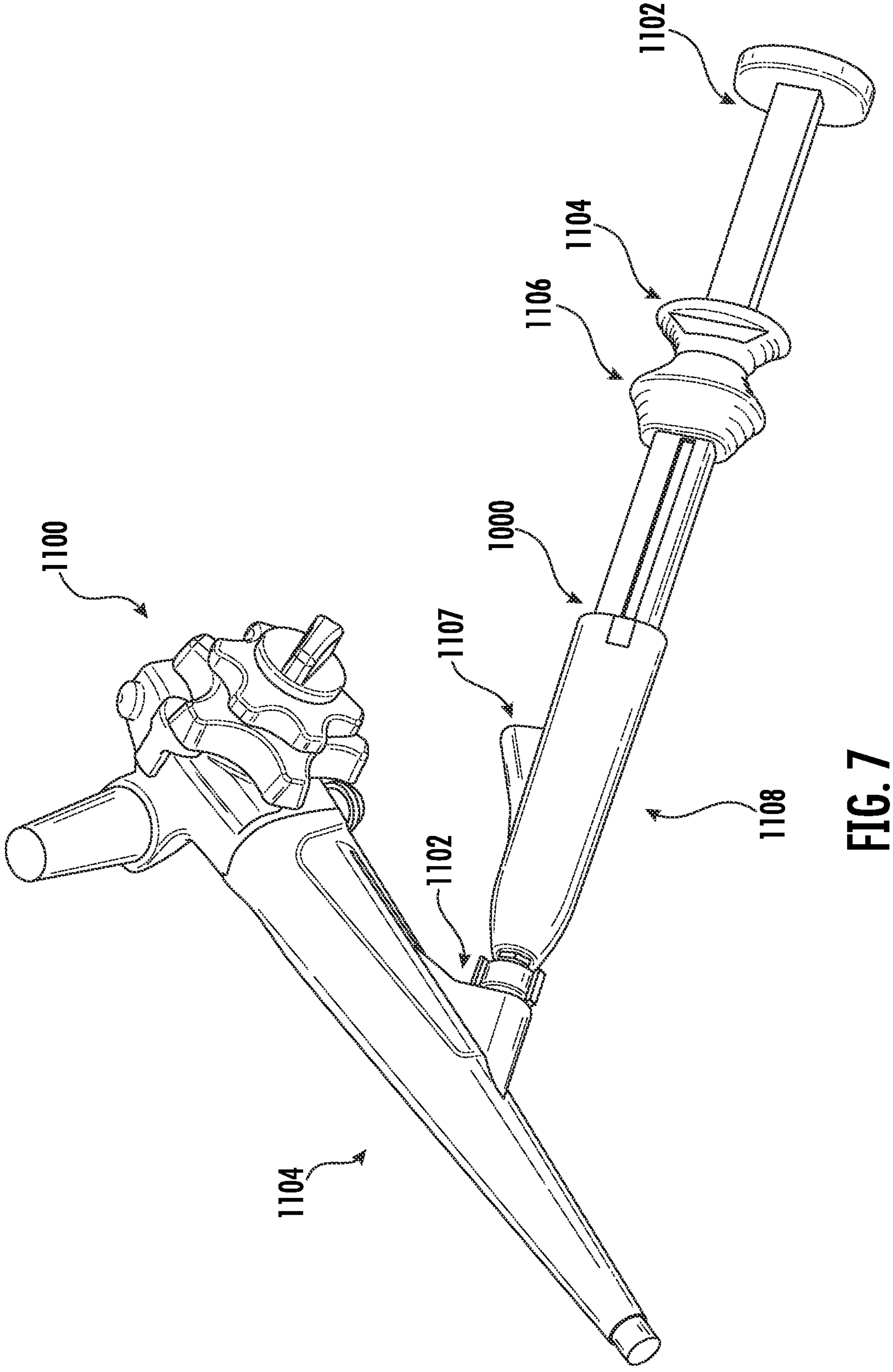
FIG. 7 illustrates a perspective view of an example of a device useful for deploying one or both of a stent and/or a functional and/or therapeutic agent according to one or more embodiments described herein.

Additionally, or alternatively, as second sheath 106 is proximally retracted together with or with respect to first sheath 104, functional and/or therapeutic agent 150 may be unsheathed from second sheath 106 and/or moved distally relative to distal end 106*d* of second sheath 106 and/or moved distally relative to distal end 104*d* of first sheath 104. Alternatively, or additionally, functional and/or therapeutic agent 150 may be distally extruded or extended from between first sheath 104 and second sheath 106. For instance, functional and/or therapeutic agent 150 may be moved distally with respect to distal end 104*d* of first sheath 104 and distal end 106*d* of second sheath 106 such as a result of pressure applied thereto from a proximally positioned pushing member (not shown), or a proximal source of air pressure, or other force which may be controlled via a control handle 1000 coupled to proximal end 100*p* of deployment system 100 (such as to a proximal end of one or more of inner member 102, first sheath 104, or second sheath 106). For example, a control handle 1000 such as illustrated in FIG. 7 (and described in further detail below) may comprise means to affect a pressurization of air proximal to functional and/or therapeutic agent 150 (e.g., into space 107), thereby effecting a distal extrusion of the functional and/or therapeutic agent 150.

Various aspects of an example of deployment of an example of an embodiment of a stent 210 are illustrated in FIGS. 2A-2D. Although stent 210 is illustrated as being formed of a braided wire, various alternative known and heretofore known constructions and/or configurations of stents are within the scope and spirit of the present disclosure. Of note, stent 210 may shift or transition between first and second configurations as described with respect to stent 110 and may be similarly disposed between inner member 102 and first sheath 104 as described with respect to FIGS. 1A-1B, with inner member 102 extending through a lumen 211 extending longitudinally through stent 210. In some embodiments, a cover may be provided over stent 210, such as described with respect to stent 110.

Figure 2A:
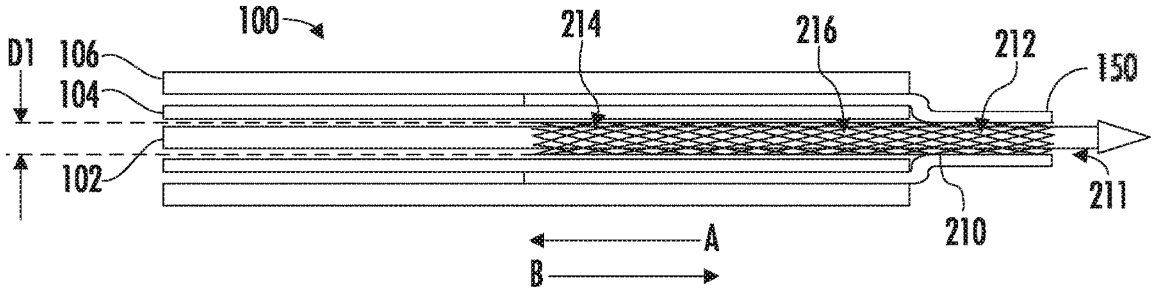
FIGS. 2A-2D illustrate examples of aspects of a deployment of a stent with a functional and/or therapeutic agent according to one or more embodiments described herein.
Figure 2B:
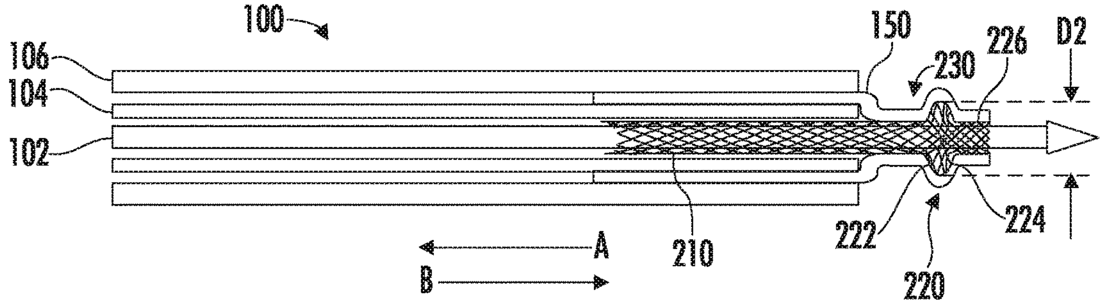
Figure 2C:
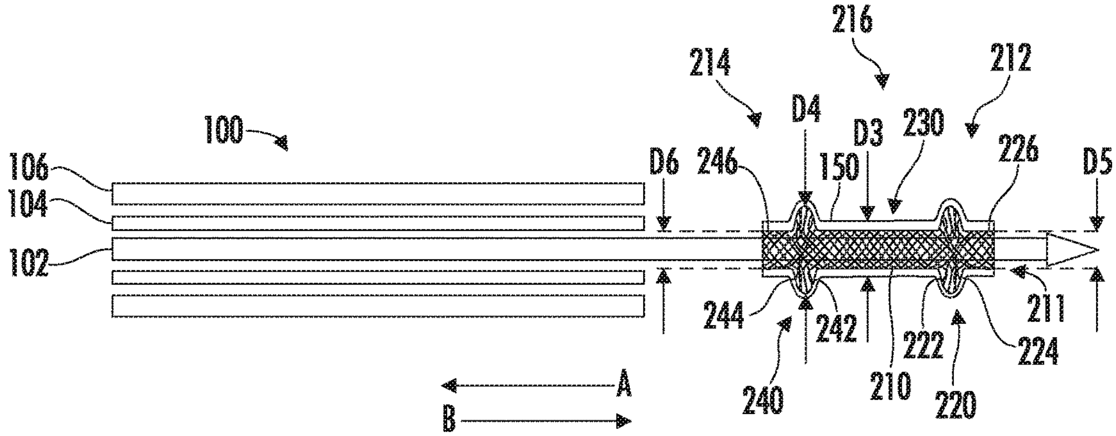
Figure 2D:
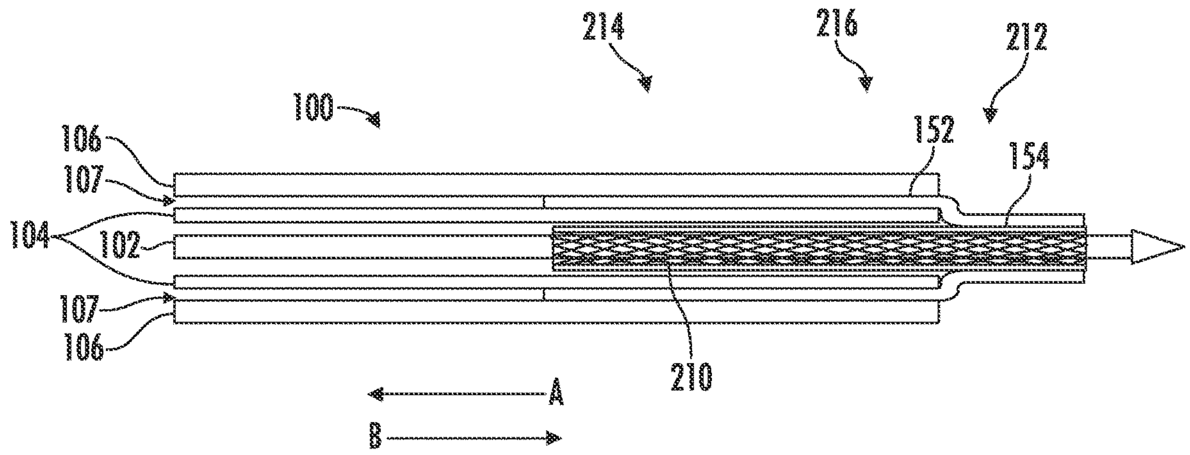

The example of a stent 210 illustrated in FIG. 2A has a first end 212, a second end 214, and a middle segment 216 extending therebetween, which may have the same or substantially the same diameters D1 in the first configuration. As may be seen in FIGS. 2A-2B, as first sheath 104 and second sheath 106 are proximally retracted in the proximal direction of arrow A with respect to inner member 102 and stent 210, and/or as inner member 102 (carrying stent 210) is distally extended in the distal direction of arrow B with respect to first sheath 104 or both first sheath 104 and second sheath 106, first end 212 of stent 210 may transition to a second configuration of stent 210 which may define a first retention member 220 along first end 212 of stent 210. In some examples, diameter D2 of first retention member 220 (of a portion of stent 210 in a second configuration) is greater than diameter D1 of first end 212 of stent 210 in the first configuration. In various embodiments, first retention member 220 may, in some examples, be a double-walled retention member having a first retention member inner wall 222 facing middle segment 216 (e.g., facing proximally) and a first retention member outer wall 224 facing away from middle segment 216 (e.g., facing distally), and generally coupled to first retention member inner wall 222, either or both of which may be configured to interface with tissue.

First sheath 104 and second sheath 106 may be further proximally retracted in the proximal direction of arrow A with respect to inner member 102, and/or inner member 102 may be distally extended in the distal direction of arrow B with respect to first sheath 104 or both first sheath 104 and second sheath 106, such that middle segment 216 forms a saddle region 230 extending proximally from first retention member 220 in the second configuration. Saddle region 230 may be generally cylindrical. Saddle region 230 may have the same or different diameter (e.g., diameter D3) as middle segment 216 in the first configuration (e.g., diameter D1). In several examples, saddle region 230 may have a larger diameter than middle segment 216 in the first configuration.

As may be seen in FIG. 2C, first sheath 104 and second sheath 106 may be even further proximally retracted in the proximal direction of arrow A with respect to inner member 102, or inner member 102 may be distally extended in the distal direction of arrow B with respect to first sheath 104, or both first sheath 104 and second sheath 106, such that second end 214 forms a second retention member 240 proximally adjacent to saddle region 230. In some examples, diameter D4 of second retention member 240 (of a portion of stent 210 in the second configuration) may be greater than diameter D1 of second end 214 of stent 210 in the first configuration. Second retention member 240 may, in some examples, be a double-walled retention member having a second retention member inner wall 242 (e.g., facing proximally) and second retention member outer wall 244 facing away from middle segment 216 (e.g., facing distally), either or both of which may be configured to interface with tissue.

First retention member 220 and second retention member 240 may have identical or different shapes, sizes, and/or configurations. For example, diameter D2 and diameter D4 may be equal in magnitude or different. In various examples, one or both of first retention member 220 and/or second retention member 240 may include a flange, for example, a double-walled flange. In other examples, first retention member 220 and/or second retention member 240 may include a ridge, bump, flare, ramp, cylindrical portion with a greater diameter than the diameter of saddle region 230, or other surface feature (not shown), which may extend fully or partially around a circumference of the stent 210. In several embodiments according to the present disclosure, diameter D2 and diameter D4 may be greater than a diameter of a cutting element (not shown, but such as cutting element 108 illustrated in FIG. 1B) such that first retention member 220 and second retention member 240 may be wider than an anastomosis formed by a cutting element.

In some examples, stent 210 may include a first lip 226, which may extend from the first retention member 220 away from saddle region 230 (e.g., extend distally). Similarly, stent 210 may include a second lip 246, which may extend from the second retention member 240 away from saddle region 230. Diameter D5 of first lip 226 and diameter D6 of second lip 246 may be the same or different diameter, and may be the same or different from diameter D3 of saddle region 230. In some embodiments, diameter D5 and/or diameter D6 is larger than diameter D3 so that stent 210 has wider openings through retention members 220, 240 at its respective ends 212, 214 than the diameter of the portion of lumen 211 extending through saddle region 230, which may facilitate greater flow of fluid through lumen 211 extending through stent 210 when in the second configuration.

As may be seen with reference to the example illustrated in FIGS. 2A-2C, functional and/or therapeutic agent 150 may be deployed and disposed along stent 210 as stent 110 deployed. For example, a positive pressure applied from proximal end 100*p* of deployment system 100 into space 107 between first sheath 104 and second sheath 106, such as actuated by handle 1000 (illustrated in FIG. 7), may be exerted on the functional and/or therapeutic agent 150, optionally in coordination with a proximal retraction of first sheath 104 and second sheath 106 with respect to inner member 102, and/or in coordination with a distal extension of inner member 102 with respect to first sheath 104 and second sheath 106, such that functional and/or therapeutic agent 150 is disposed along a portion of stent 210 (e.g., along one or more of first end 212, middle segment 216, or second end 214) as stent 210 is distally released from within or unsheathed from first sheath 104. In some examples and as illustrated in FIGS. 2A-2C, a layer of functional and/or therapeutic agent 150 may thus be deposited along a portion of or along an entire outer surface of stent 210 (such as illustrated, for example, in FIG. 3A or FIG. 3B).

Figure 3A:
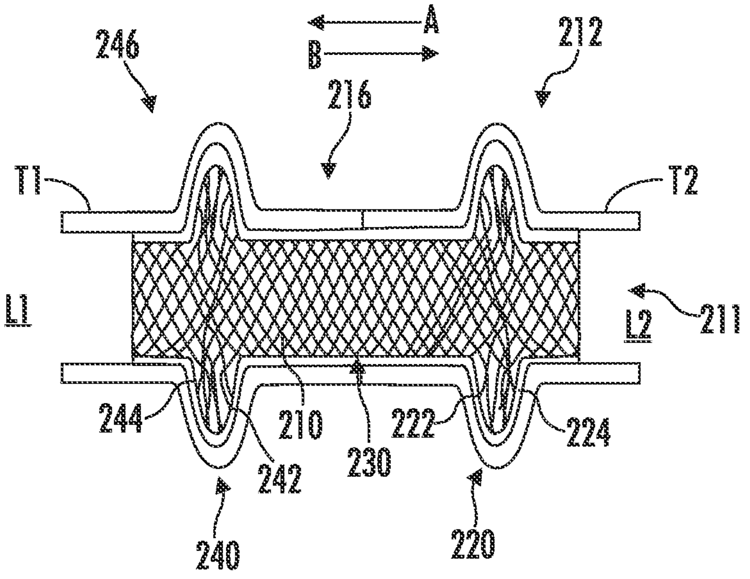
FIG. 3A provides a cross-sectional view of a end-to-end anastomosis formed with a stent with a functional and/or therapeutic agent according to one or more embodiments described herein.
Figure 3B:
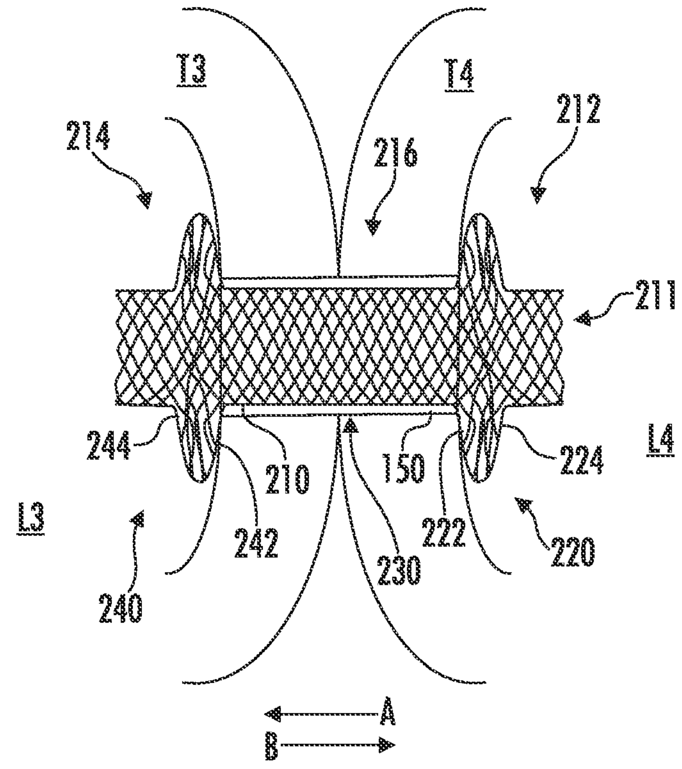
FIG. 3B provides a cross-sectional view of a stent with a functional and/or therapeutic agent bridging apposed tissue walls according to one or more embodiments described herein.

In other examples, a positive pressure applied from proximal end 100*p* of deployment system 100 into space 107 between first sheath 104 and second sheath 106 may be effected via handle 1000 (illustrated in FIG. 7) so as to selectively and/or partially dispose functional and/or therapeutic agent 150 along stent 210. For example, functional and/or therapeutic agent 150 may be disposed such that an entirety or part of one or more of lip 226, first retention member outer wall 224, first retention member 220, first retention member inner wall 222, saddle region 230, second retention member inner wall 242, second retention member 240, second retention member outer wall 244, or lip 246 is not covered with a layer of functional and/or therapeutic agent 150 once deployed. In other words, functional and/or therapeutic agent 150 may intermittently or discontinuously or partially cover stent 210. For example, stent 210 as illustrated in FIG. 3B includes functional and/or therapeutic agent 150 disposed only along saddle region 230. In other embodiments, not illustrated for the sake of simplicity (such concepts being readily understood by those of ordinary skill in the art), functional and/or therapeutic agent 150 may be disposed along each of first retention member 220 and second retention member 240 but not along saddle region 230, along saddle region 230 and first retention member inner wall 222 and second retention member inner wall 242 only, along lip 226 and first retention member 220, along lip 246 and second retention member 240, or along any other combination(s) of lip 226, first retention member outer wall 224, first retention member 220, first retention member inner wall 222, saddle region 230, second retention member inner wall 242, second retention member 240, second retention member outer wall 244, or lip 246.

It will be understood that, in the event that stent 210 comprises a cover (not shown for the sake of simplicity in the drawings), the cover may be helpful in preventing functional and/or therapeutic agent 150 from flowing through one or more holes of a porous surface (e.g., gaps in the braided weave) of stent 210 and into lumen 211. Accordingly, a cover may be helpful in maintaining a position of functional and/or therapeutic agent 150 along the surface of stent 110. Stent 210 may comprise a full cover or a partial cover. For example, a partial cover may include one or more segments of a cover along its length in areas in which a presence of functional and/or therapeutic agent 150 is desirable, with remaining portions of stent 210 not comprising a cover (thus allowing functional and/or therapeutic agent 150 to flow or drain through a porous surface of stent 210, for example, or functional and/or therapeutic agent 150 not being provided along such portion of stent 110). In some embodiments, one or more markers along stent 210 may indicate a start or an end of a partial cover (not shown) or other region along stent 210 so as to indicate where functional and/or therapeutic agent 150 should be disposed. Accordingly, excess use of functional and/or therapeutic agent 150 may be minimized, which may reduce an amount of functional and/or therapeutic agent 150 needed for an initial loading of functional and/or therapeutic agent 150 between first sheath 104 and second sheath 106, and/or which may minimize an amount of functional and/or therapeutic agent 150 which flows into a patient's body. In some embodiments, the functional and/or therapeutic agent 150 may be laid down before and/or after positioning and deployment of the stent 210, such as to act as a buffer (e.g., for regions of lesions that might be longer than stent 210).

Functional and/or therapeutic agent 150 may be disposed along one or more portions of stent 210 such that a respective diameter along stent 210 is increased in magnitude above diameter D1, diameter D2, diameter D3, diameter D4, diameter D5, or diameter D6, although in various embodiments functional and/or therapeutic agent 150 may be disposed along stent 210 so as to not substantially increase a respective diameter of stent 210. Embodiments are not limited in this context.

Functional and/or therapeutic agent 150 may in some embodiments comprise a curable agent such as an adhesive, which may cure automatically over time, such as with exposure to biological tissue or body temperature, or based on an external stimulus. For example, functional and/or therapeutic agent 150 may cure based on an exposure to UV light, for example, from a light extended through a working channel of control handle 1000 as illustrated in FIG. 7.

In some embodiments, functional and/or therapeutic agent 150 may comprise multiple components, which, when in contact with each other, effect a curing and/or polymerization process. For example, functional and/or therapeutic agent 150 may comprise a fibrin glue, in which a first component may comprise thrombin and a second component may comprise fibrinogen. In some examples in which functional and/or therapeutic agent 150 comprises multiple components, particularly which may be reactive with each other, a first functional and/or therapeutic agent component 152 may be disposed in space 107 between first sheath 104 and second sheath 106 (such as in an inactive state), and a second functional and/or therapeutic agent component 154 may be disposed along a surface of stent 210 prior to deployment.

As illustrated in FIG. 2D, rather than a complete, active form of functional and/or therapeutic agent 150 (such as described with respect to FIGS. 2A-2C), an example of a first functional and/or therapeutic agent component 152 is illustrated disposed in space 107 between first sheath 104 and second sheath 106, and may be disposed (e.g., deposited) along stent 210 similarly as functional and/or therapeutic agent 150 along stent 210 as described above with respect to FIGS. 2A-2C. However, unlike the example illustrated in FIGS. 2A-2C, stent 210 has second functional and/or therapeutic agent component 154 along all or a portion thereof (first end 212, second end 214, and/or middle segment 216) before deployment. Accordingly, as first functional and/or therapeutic agent component 152 is deposited over stent 210 first functional and/or therapeutic agent component 152 may be deposited over second functional and/or therapeutic agent component 154 already in place over stent 110, and first functional and/or therapeutic agent component 152 and second functional and/or therapeutic agent component 154 may react with each other, such as to polymerize in-situ. Embodiments are not limited in this context.

While not shown in FIGS. 2A-2D for the sake of simplicity, stents 210 may be deployed across one or more tissues, body lumens, or the like, such as to create a flow path therebetween and/or to join tissues. For example, as shown in FIG. 3A, an example of an embodiment of a stent 210, such as illustrated in the examples of FIGS. 2A-2D, may be used to create end-to-end anastomoses. As shown in FIG. 3B, an example of an embodiment of a stent 210, such as illustrated in the examples of FIGS. 2A-2D, may be used to create side-to-side anastomoses.

As illustrated in FIG. 3A, stent 210 may be deployed from deployment system 100 (such as described with respect to FIGS. 2A-2D) to extend across and through body lumen L1 and body lumen L2, respectively defined by tissue T1 and tissue T2. For example, tissue T1 and tissue T2 may be blood vessels, sections of intestine, or other tissue. In some embodiments, deployment of a first retention member 220 as described above may be within body lumen L2. For example, deployment system 100 may be introduced through body lumen L1 and extended to or into body lumen L2 (not shown). In this example, first sheath 104 and second sheath 106 may be proximally retracted with respect to inner member 102 while all three are disposed within body lumen L2, and/or inner member 102 may be distally extended with respect to first sheath 104 and second sheath 106 into body lumen L2. In any event, first end 212 may transition into first retention member 220 within body lumen L2, particularly such that first retention member 220 engages with an inner surface of tissue T2, thereby lodging, securing, anchoring, or otherwise retaining a position of a first end 212 of stent 210 within body lumen L2. Deployment system 100 may be proximally retracted (together with first end 212), for example, in the direction of arrow A, such that tissue T2 is moved with deployment system 100 and stent 210 and brought into apposition with tissue T1. Next, second retention member 240 may be deployed within body lumen L1, for example, via steps described above, such that second retention member 240 contacts tissue T1 so as to be secured, lodged, or otherwise retained within body lumen L1. Functional and/or therapeutic agent 150 may serve, in many cases, to increase a retentive strength of the anastomosis facilitated by stent 210, such as by adhering to one or both of tissue T1 or tissue T2 and/or causing tissue T1 and tissue T2 to adhere to each other (such as in examples in which tissue T1 and tissue T2 form an end-to-end anastomosis).

In the example illustrated in FIG. 3B, stents 210 may be used to facilitate drainage from one organ or body lumen into another organ or lumen. For example, a cutting element 108 (such as illustrated in FIG. 1B) may be distally advanced in the direction of arrow B from body lumen L3, through tissue T3, through tissue T4, and into body lumen L4. First retention member 220 may then be deployed within body lumen L4 according to one or more aspects described above. In some examples, deployment system 100 (together with first retention member 220) is distally advanced such that tissue T4 is brought into apposition with tissue T3. Next, second retention member 240 may be deployed within body lumen L3, for example, via steps described above, such that second retention member 240 contacts tissue T3 so as to be secured, lodged, or otherwise retained within body lumen L3. In some embodiments, functional and/or therapeutic agent 150 may adhere to one or both of tissue T3 or tissue T4, such as to hold tissue T3 and tissue T4 in apposition with each other and stent 110. For instance, saddle region 230 may extend across tissue T3 and tissue T4 and functional and/or therapeutic agent 150 along saddle region 230 may adhere to both tissue T3 and tissue T4.

It will be appreciated that principles of the present disclosure with respect to delivery and deployment of a functional and/or therapeutic agent 150 need not be limited to anastomoses. For example, as illustrated in FIGS. 4A-4E, a stent 310 may be positioned within a body lumen L5, such as an intact or single body lumen L5, to deliver or otherwise to provide a functional and/or therapeutic agent 150 with respect to tissue. For instance, an obstruction in a lumen may be opened by a stent 510, and/or a functional and/or therapeutic agent 150 may be delivered to an affected area (e.g., diseased, damaged, etc.) along a lumen. Stent 310 may share one or more features or aspects of stents 110, 210 described above. For instance, a cover (such as a silicone cover or coating) may be provided over stent 310. Stent 310 may have a first end 312 along which a first retention member 320 may be formed or provided, a second end 314 along which a second retention member 340 may be formed or provided, and a middle segment 316 along which a saddle region 330 extends. A functional and/or therapeutic agent 150 may be associated with stent 310. In some embodiments, functional and/or therapeutic agent 150 is provided along saddle region 330 and longitudinally between first retention member 320 and second retention member 340, and stent 310 is disposed with functional and/or therapeutic agent 150 positioned along tissue T5 with an area to be treated. The functional and/or therapeutic agent 150 may be associated with stent 310 in any of a variety of manners as described above. For instance, functional and/or therapeutic agent 150 may be positioned on stent 310 as stent 310 is deployed, and/or may be provided in the form of one or more functional and/or therapeutic agent components, at least one of which is provided on stent 310 prior to deployment, such as prior to delivery, and at least another of which is provided on stent 310 during deployment to cause activation of functional and/or therapeutic agent 150 at the deployment site. Additionally or alternatively, functional and/or therapeutic agent 150 may be provided after stent 310 has been deployed. Stent 310 may be configured to hold additional, or alternative, functional and/or therapeutic agent 150 along its saddle region 330. For example, first retention member 320 and second retention member 340 may hold tissue T5 spaced away from saddle region 330 so as to create a working space into which functional and/or therapeutic agent 150 may be injected after deployment of stent 310, for example, according to methods as discussed below.

Figure 4A:
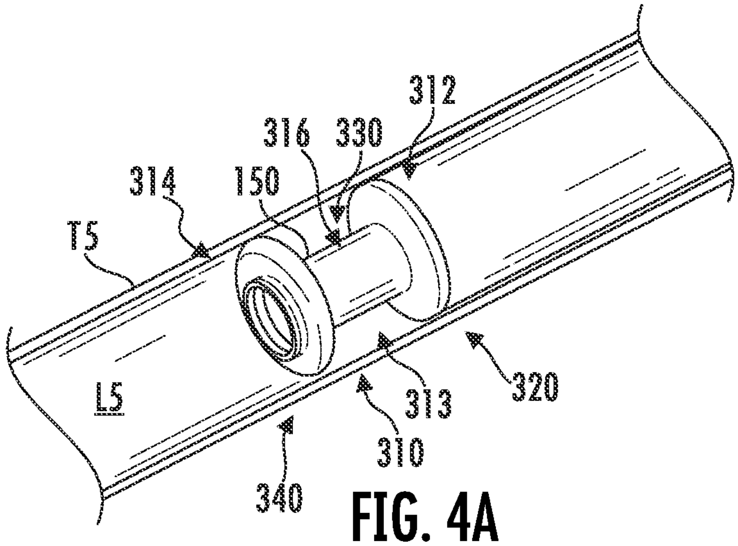
FIG. 4A illustrates an example of a stent according to one or more embodiments described herein deployed in a body lumen.
Figure 4B:
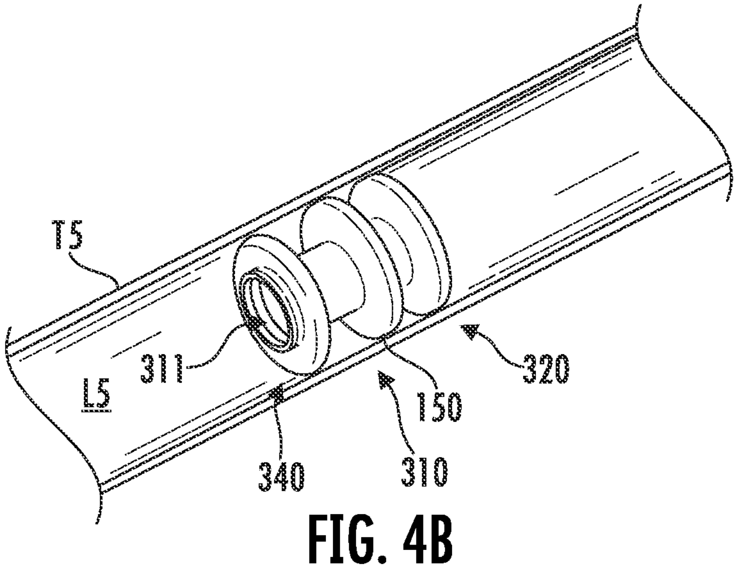
FIGS. 4B-4E illustrate various examples of a stent as in FIG. 4A with a functional and/or therapeutic agent deployed thereon according to one or more embodiments described herein.
Figure 4C:
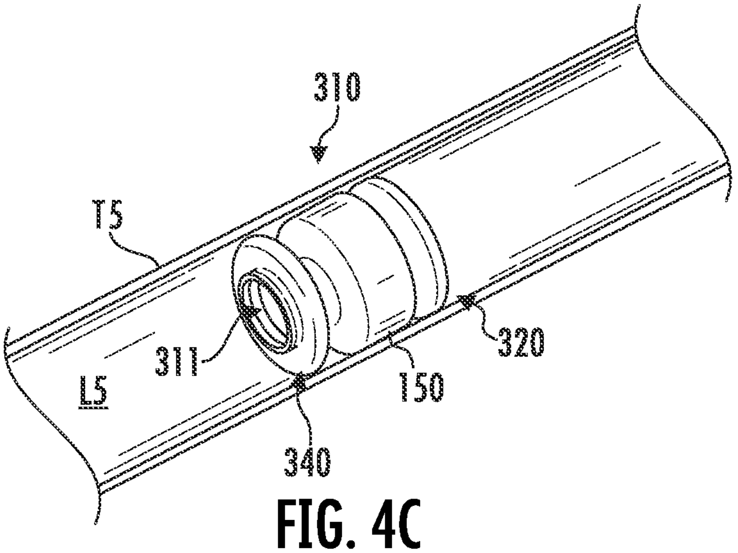
Figure 4D:
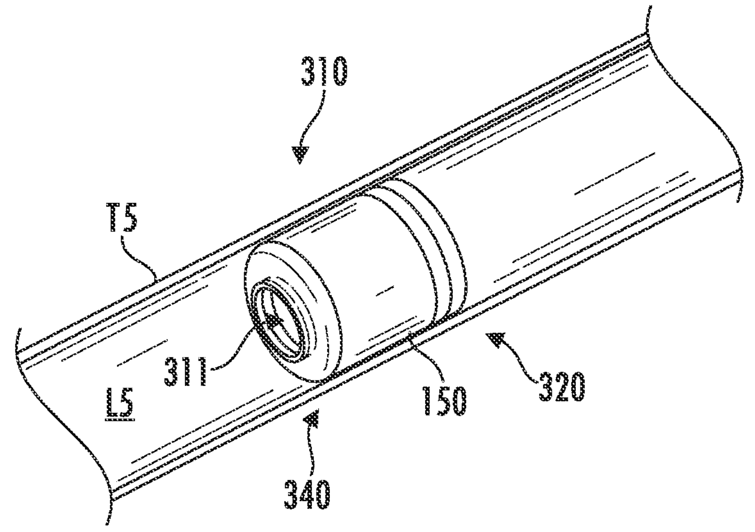
Figure 4E:
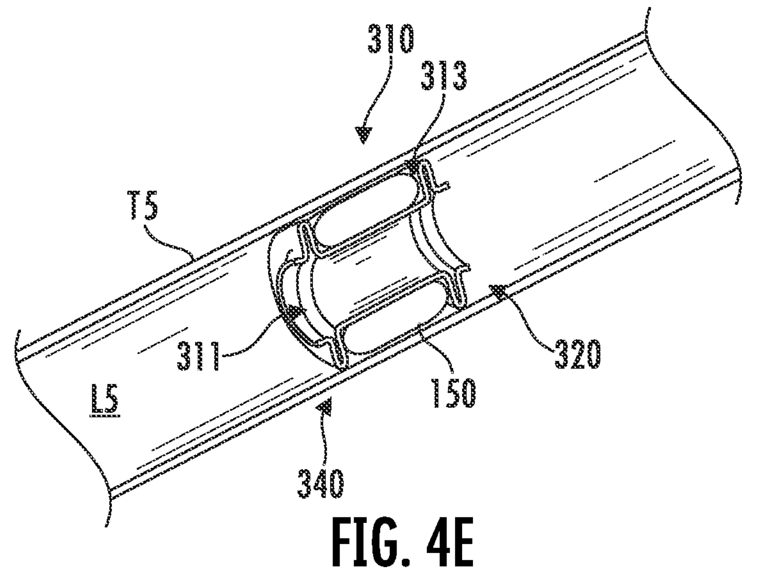

Functional and/or therapeutic agent 150 may be provided along saddle region 330 of stent 310 in incremental and/or predetermined volumes such that volume 313, defined by saddle region 330, first retention member 320, second retention member 340, and tissue T5 (tissue forming the wall of lumen L5 in which stent 310 is positioned), as illustrated in FIG. 4A, may be filled with various percentages of functional and/or therapeutic agent 150. For example, FIGS. 4B and 4C illustrate respectively larger volumes of functional and/or therapeutic agent 150 injected along saddle region 330 between first retention member 320 and second retention member 340. FIG. 4D illustrates an example in which substantially the entire volume 313 defined by saddle region 330, first retention member 320, second retention member 340, and tissue T5 has been filled with functional and/or therapeutic agent 150. FIG. 4E illustrates a cross-sectional view of the example illustrated in FIG. 4D, illustrating that lumen 311 of stent 310 may be maintained through stent 310, for example, by the effectiveness of a cover over stent 310 retaining functional and/or therapeutic agent 150 within volume 313 and inhibiting flow of functional and/or therapeutic agent 150 through the stent 310 wall into lumen 311. It will be appreciated that FIGS. 4A-4E may be viewed as sequentially illustrating different stages of delivery of a functional and/or therapeutic agent 150, or each of FIGS. 4A-4E may be viewed as illustrating a stent 310 with a different volume of functional and/or therapeutic agent 150 already delivered thereto. In any or all of the examples of embodiments illustrated in FIGS. 4A-4E, the functional and/or therapeutic agent 150 may be in any desired weight per volume of delivery agent or carrier as indicated to achieve the desired functional and/or therapeutic effect with the appropriate viscosity value. For instance, the functional and/or therapeutic agent 150 may be suspended or compounded in the delivery agent or carrier at a desired weight per volume of delivery agent or carrier.

In some embodiments, stent 310 may be disposed within a lumen L5 having a tissue area to be treated. Saddle region 330 of stent 310 may be positioned along tissue T5 with the tissue area to be treated positioned longitudinally between first retention member 320 and second retention member 340. Functional and/or therapeutic agent 150 may be provided in a gel or liquid form and contained within volume 313 and retained in place adjacent the tissue area to be treated. For instance, a cover over stent 310 (such as described above) may retain functional and/or therapeutic agent 150 within volume 313 without allowing functional and/or therapeutic agent 150 to seep out from volume 313.

In some embodiments, functional and/or therapeutic agent 150, positioned within volume 313, may comprise an agent as described above. For instance, functional and/or therapeutic agent 150 may include one or more healing agents, for example, growth factors, anti-inflammatory agents, or the like, which may aid in a healing of tissue T5. In some embodiments, functional and/or therapeutic agent 150 may comprise a first functional and/or therapeutic agent component 152 and a second functional and/or therapeutic agent component 154 delivered separately to the deployment site. For example, a second functional and/or therapeutic agent component 154 may be delivered with stent 310 and a first functional and/or therapeutic agent component 152 delivered separate from stent 310 and deployed with stent 310 such as into contact with the second functional and/or therapeutic agent component 154. In some embodiments, additional amounts of functional and/or therapeutic agent 150, or first functional and/or therapeutic agent component 152 and second functional and/or therapeutic agent component 154, may be deployed into volume 313 after stent 310 has been deployed in lumen L5 (as described in further detail below). Functional and/or therapeutic agent 150 may comprise at least one additionally adhesive component. For example, after deployment of stents 310, a medical professional may determine that additional adhesion of stent 310 with respect to surrounding tissue may be desirable, in which case functional and/or therapeutic agent 150 may be provided after stent 310 has already been deployed, as described in further detail below. Embodiments are not limited in this context.

Figure 5A:
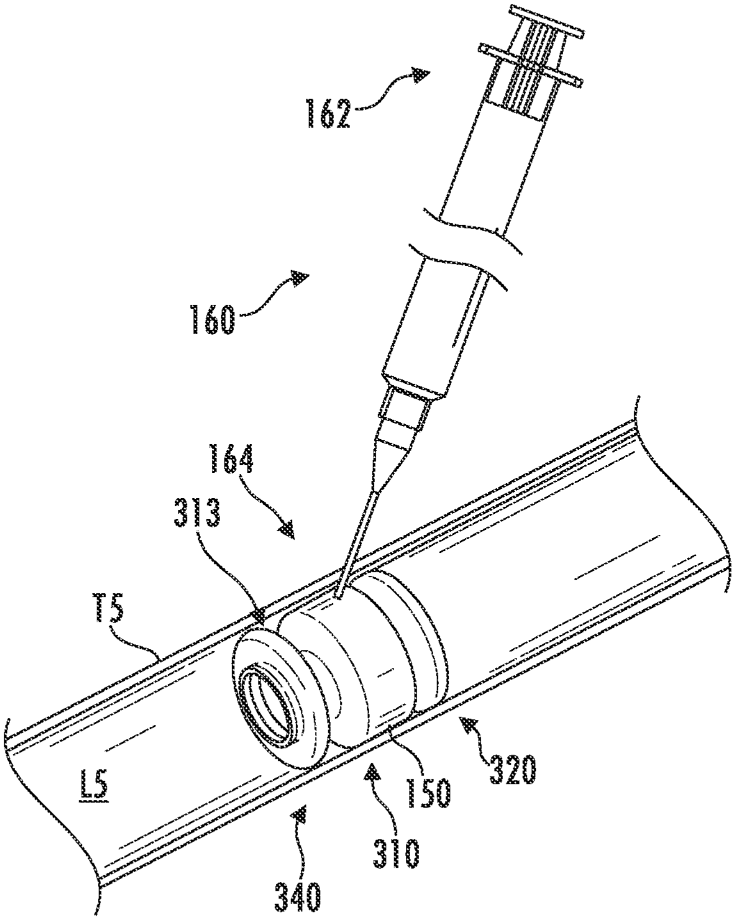
FIG. 5A illustrates a percutaneous injection of a functional and/or therapeutic agent along a surface of a deployed stent according to one or more embodiments described herein.
Figure 5B:
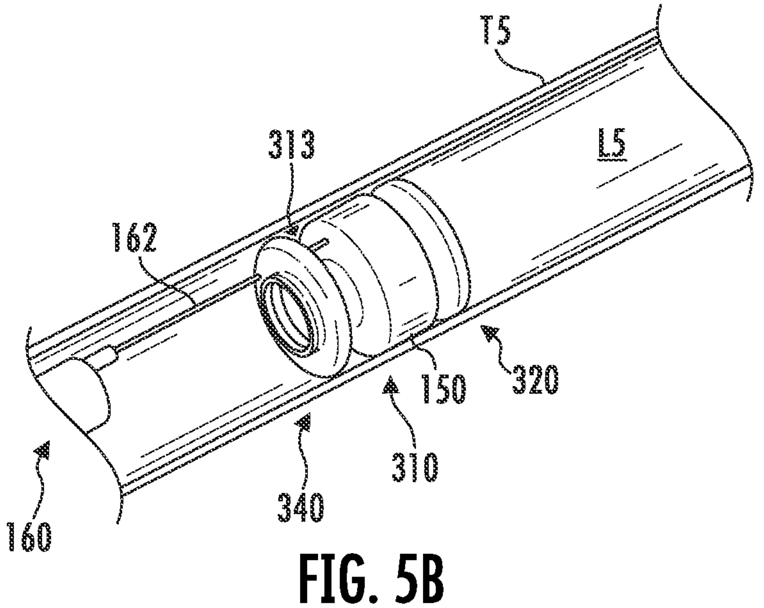
FIG. 5B illustrates an intraluminal or intraductal injection of a functional and/or therapeutic agent along a surface of a deployed stent according to one or more embodiments described herein.

If functional and/or therapeutic agent 150, or first functional and/or therapeutic agent component 152 and second functional and/or therapeutic agent component 154, are not deployed with or when stent 310 is deployed, such as described above, a stent configured as stent 310 (e.g., with a retention member along each end and a saddle region therebetween) may permit later deployment of a functional and/or therapeutic agent or one or more components of a functional and/or therapeutic agent with respect to the stent and the lumen in which the stent is positioned, such as stent 310 within lumen L5 as illustrated in FIG. 5A and FIG. 5B. In some embodiments, a functional and/or therapeutic agent or one or more components of functional and/or therapeutic agent may be injected into volume 313 defined by saddle region 330, first retention member 320, second retention member 340, and tissue T5. As illustrated in FIG. 5A, a fluid delivery device 160, such as a syringe or hypodermic needle or the like, may be used to deliver functional and/or therapeutic agent 150 percutaneously through the wall of lumen L5 and into volume 313 between the stent 310 and the lumen L5. Fluid delivery device 160 may be any desired shape or configuration and may have the necessary length to reach the treatment site at lumen L5 percutaneously, as may readily be understood by those of ordinary skill in the art. For instance, functional and/or therapeutic agent may be dosed at a proximal dosage controller 162 and injected through tissue penetrating end 164 through the tissue T5 and into volume 313. Additionally or alternatively, in some embodiments, a functional and/or therapeutic agent or one or more components of a functional and/or therapeutic agent may be injected into volume 313 through a wall of stent 310, such as illustrated in FIG. 5B. For instance, a fluid delivery device 160 may be delivered transluminally through lumen L5 to the deployment site of stent 310. In some embodiments, the walls of stent 310 (such as the walls of one of the retention members 320, 340) may be penetrable by tissue penetrating end 164 of fluid delivery device 160 so that a desired amount of functional and/or therapeutic agent may be dosed therethrough (e.g., from a proximal end of the fluid delivery device 160, such as along a control handle 12 of a delivery and deployment device 10 as illustrated in FIG. 7). As described above, a cover may be provided over stent 310 and may retain functional and/or therapeutic agent within volume 313. Such cover may be penetrable by tissue penetrating end 164 of fluid delivery device 160 and self-sealing upon withdrawal of tissue penetrating end 164 to retain functional and/or therapeutic agent within volume 313.

Figure 6:
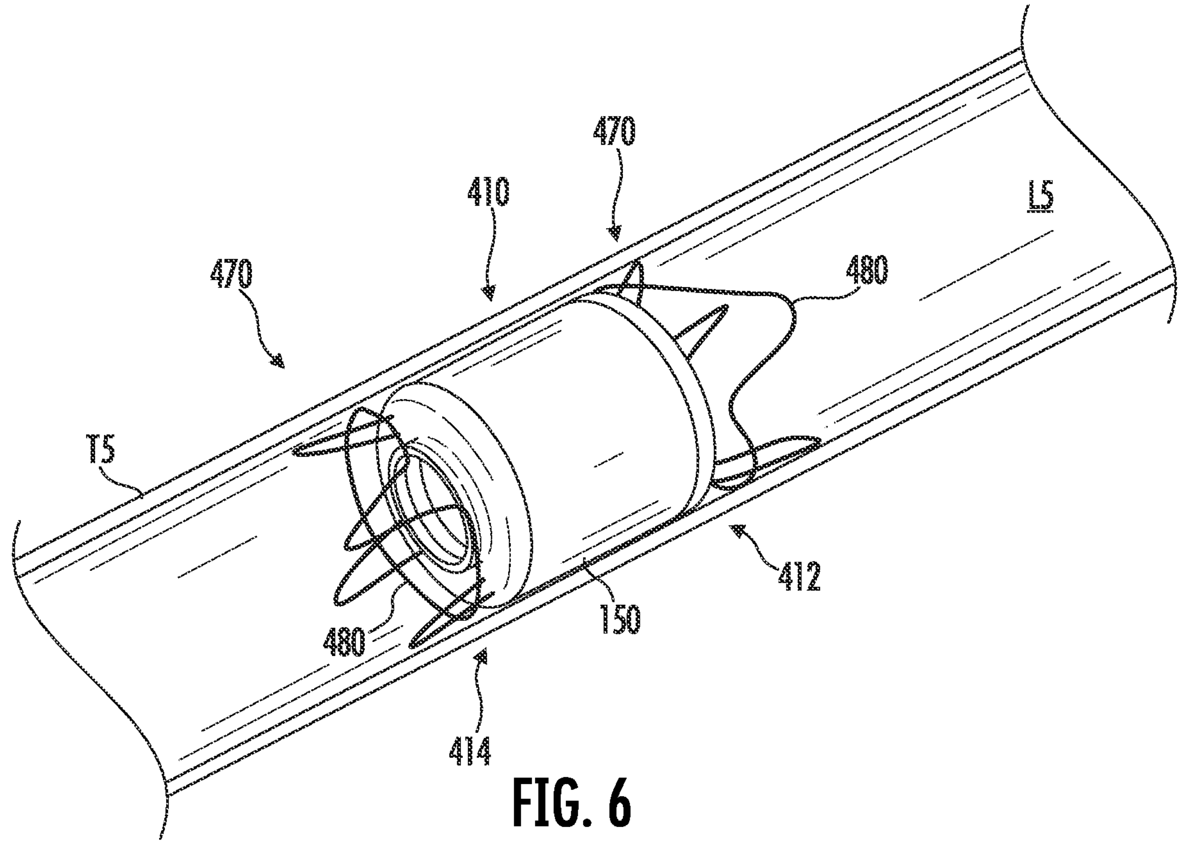
FIG. 6 illustrates a perspective view of an example of a deployed stent with a functional and/or therapeutic agent and retention prongs according to one or more embodiments described herein.

In some embodiments, as described above, a functional and/or therapeutic agent 150 with an adhesive agent may be provided within a volume 313 defined between stent 310 and lumen L5 to inhibit migration of stent 310 with respect to tissue T5. In some embodiments, it may be desirable to provide mechanical retention or anti-migration features instead of or in addition to material or chemical-based retention agents (such as adhesive agents). For instance, functional and/or therapeutic agent 150 may not contain an adhesive agent, and/or additional retention features may be necessary if forces at the deployment site are thought at times to overcome adhesive properties of functional and/or therapeutic agent 150 and/or the retentive forces applied by the retention flanges of the stent. It will be appreciated that a stent as configured in any or all of FIGS. 4A-4E, 5A, 5B may be covered or coated to prevent seepage or leakage of a functional and/or therapeutic agent 150 deployed within the volume defined by the inner walls of the retention members and the outer surface of the saddle region thereof. Such cover generally resists tissue ingrowth, and thus may not inhibit migration of the stent. In accordance with various principles of the present disclosure in some embodiments, as illustrated in FIG. 6, an embodiment of a stent 410 may be provided with additional mechanical anchoring elements. The anchoring elements may be in the form of one or more anchors 470 along stent 410, such as along first end 412 and/or second end 414 of stent 410. Anchors 470 may be in any desired form, such as loop-shaped projections or fins (as illustrated), or posts, quills, spikes, barbs, hooks, etc., such as known or heretofore known in the art to facilitate anchoring of a device, such as a stent, with respect to tissue to inhibit/prevent migration of the device relative to the tissue. Anchors 470 may be formed of resilient biocompatible materials such as metals or polymers, such as wires similar to those forming the stent 410. Anchors 470 may be used to remove stent 410, such as by pulling on one or more of anchors 470. Additionally or alternatively, a removal/retrieval device 480, such as a filament, a cord, a suture, a wire, a string, a band, etc., may be provided along or about a circumference of anchors 470 and/or an end 412, 414 of stent 410 to facilitate removal of stent 410, if desired, in a manner known or heretofore known in the art. Retrieval device 480 may be configured and positioned with respect to stent 410 (e.g., interwoven with the wall of stent 410) such that pulling of removal device 480 cinches or contracts stent 410 to facilitate removal of stent 410. For instance, retrieval device 480 may be in the form of a suture retrieval loop that passes through both stent 410 and anchors 470 in a manner that pulls in anchors 470 and collapses stent 410 when retrieval device 480 is pulled, allowing stent 410 to be removed from the deployment site.

Deployment system 100 may be delivered to a treatment site via an endoscope 1100 such as illustrated in FIG. 7. Endoscope 1100 may be any of a number of types of endoscopes or related medical devices, usually selected based on the particular anatomy desired to be reached, such as a colonoscope, duodenoscope, bronchoscope, gastroscope, or ureteroscope, or similar medical device. Deployment system 100 may inserted through a port 1102 in the handle 1104 of endoscope 1000 and a working channel through flexible elongate shaft 1108. A deployable scaffold, such as known or heretofore known, may be provided at a distal end of elongate shaft 1108, and may be positioned and subsequently expanded within a body lumen to improve access to and/or visualization of a target tissue/treatment site by the endoscope and/or a tool thereof. Endoscope 1100 may include any of a variety of visualization components, such as an optical cable connected to an external light source (not shown). An imaging element, such as a charge coupled device (CCD) camera can be disposed at the distal end to enable a user to visualize a working area. Various additional ports may be provided along endoscope handle 1104 for delivery of other tools, application of suction, delivery of fluid (e.g., air, water, saline, functional and/or therapeutic agents, etc.), etc., as known or heretofore known. Endoscope 1000 may comprise one or more additional controls, such as knobs, which may be operative to cause articulation of one or more components thereof. Articulation, for example, may include proximal retraction, distal extension, rotation about a longitudinal axis, movement along a lateral axis, movement along a transverse axis, or any combination thereof.

In general, the delivery and deployment device 10 may include a control handle 1000 to facilitate use of deployment system 100 for treating tissue according to embodiments described herein. Control handle 1000 may comprise one or more controls, such as actuators 1002, 1004, 1006, which may be coupled, respectively, to inner member 102, first sheath 104 and second sheath 106, and operative to cause the desired distal advancement/extension or proximal retraction or other movement (e.g., rotation) or combination of movements of inner member 102, first sheath 104 and second sheath 106. An access port 1007 may be positioned along the control handle 1000 to facilitate introduction of pressure through the deployment system 100 to advance functional and/or therapeutic agent 150 (such as through space 107 between first sheath 104 and second sheath 106), and/or to introduce additional functional and/or therapeutic agents or components thereof to a stent formed in accordance with various principles of the present disclosure. Additional ports for introducing pressure, fluids (e.g., for aspiration), or other agents (e.g., imaging materials such as contrast agents) may be provided as well, such as in fluid communication with a lumen through the inner member 102.

Figure 8A:
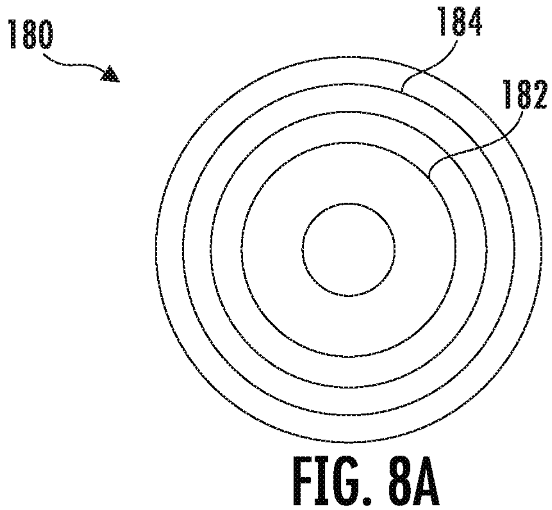
FIGS. 8A-8B illustrate top and perspective views of a delivery system end cap according to one or more embodiments described herein.
Figure 8B:
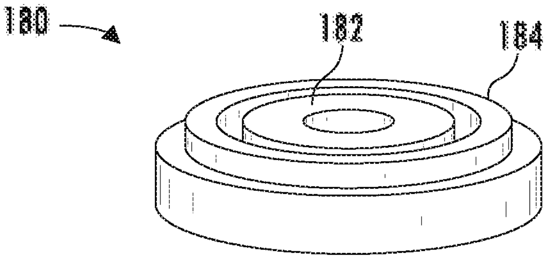

As briefly described above, a cap 180 may be provided along distal end 100*d* of deployment system 100 such as by being fitted to distal end 104*d* of at least first sheath 104 and/or distal end 106*d* of second sheath 106 prior to a procedure and/or until a practitioner is ready to release functional and/or therapeutic agent 150. An example of an embodiment of a cap 180 is illustrated in FIGS. 8A-8B according to various embodiments of the present disclosure. Cap 180 may be made with a flexible and/or inflexible material, and may be disposable (e.g., single-use) or sterilizable and reusable.

In various embodiments, cap 180 may be configured to form an interference fit with one or more cavities at the distal end of deployment system 100. For example, ridge 182 may be configured to form an interference fit between inner member 102 and first sheath 104 as described with respect to FIGS. 1A-1B, and/or ridge 184 may be configured to form an interference fit between first sheath 104 and second sheath 106. While not illustrated for the sake of simplicity in the drawings, alternatively configured attachment methods and mechanisms for caps are contemplated. For example, a cap may extend around a distal end of a deployment system 100 (e.g., around an outer diameter of second sheath 106) and/or fit to one or more aspects of the distal end of the deployment system 100 via a screw fit, luer lock, or the like.

In various embodiments, cap 180 may be removed from a distal end of a deployment system 100 prior to introduction of the deployment system 100 into a body. In other embodiments, a deployment system 100 may be advanced into a body with cap 180 still coupled to its distal end, and cap 180 may be removed during a procedure, for example, by distal extension of inner member 102 with respect to first sheath 104 and/or second sheath 106. Cap 180 may be subsequently removed from the body, for example, via a grasper (not shown). For example, if cap 180 is made of a sufficiently pliable material, cap 180 may be bent so as to have a smaller diameter than and be removable through a passage through stent 110 (through which inner member 102 extends) and through first sheath 104 and second sheath 106. Alternatively, cap 180 may be bioabsorbable, or may be passed naturally through the body. Accordingly, cap 180 may be retained on an end of deployment system 100 until a time in a procedure at which disposition of functional and/or therapeutic agent 150 is desirable, although it will be understood that in some examples, functional and/or therapeutic agent 150 may be retained within deployment system 100 after removal of cap 180, for example, by an effecting of a negative pressure proximally to functional and/or therapeutic agent 150 in working channel 16. Embodiments are not limited in this context.

Embodiments described herein may comprise various dimensions for suitability for use in various applications. A device formed in accordance with various principles of the present disclosure may have a length, in a collapsed configuration, of at least about 14 mm, or as long as 40 mm, or as long as 60 mm, or as long as about 80 mm, or as long as about 100 mm, or as long as about 150 mm, or even as long as 200 mm, including lengths in increments of 1 mm therebetween. The diameter of a device formed in accordance with various principles of the present disclosure, when in a collapsed configuration, may be as small as about 3 mm, or even as small as about 2.5 mm, and as large as about 5 mm, or as large as about 6 mm, or as large as about 10 mm, including diameters in increments of 0.5 mm therebetween. In an expanded configuration, a device formed in accordance with various principles of the present disclosure may have a length of as short as about 14 mm, or as short as about 10 mm, and as long as about 35 mm, or as long as about 50 mm, or as long as about 60 mm, or as long as about 80 mm, or as long as about 100 mm, or as long as about 120 mm, or as long as about 140 mm, or as long as about 160 mm, or as long as about 180 mm, or even as long as about 200 mm, including lengths in increments of 1 mm therebetween. The diameter of the saddle of a device formed in accordance with various principles of the present disclosure, when in an expanded configuration, may be as large as about 20 mm, or as large as about 25 mm, or as large as about 30 mm, or as large as about 35 mm, or as large as about 40 mm, or even as large as about 60 mm, and may be as small as about 10 mm, or as small as about 6 mm, or even as small as about 3 mm, including diameters in increments of 0.5 mm therebetween. The length of a saddle of a device formed in accordance with various principles of the present disclosure, when in an expanded configuration, may be as long as about 10 mm, or as long as about 15 mm, or as long as about 20 mm, or as long as about 30 mm, or as long as about 35 mm, or even as long as about 200 mm, and may be as short as about 10 mm, or as short as about 5 mm, or even as short as about 3 mm, including lengths in increments of 1 mm therebetween. In the expanded configuration, the retention members of a device formed in accordance with various principles of the present disclosure may have a diameter of as large as about 21 mm, or as large as about 24 mm, or as large as about 29 mm, or as large as about 35 mm, or as large as about 40 mm, or even as large as about 60 mm, and as small as about 16 mm, or as small as about 14 mm, or even as small as about 5 mm; and a length of as long as about 6 mm, or as long as about 7 mm, or as long as about 10 mm, including diameters and lengths in increments of 0.5 mm therebetween, and as short as about 3 mm, or as short as about 2 mm, or even as short as about 0.5 mm. A device formed in accordance with various principles of the present disclosure may have a diameter, in an expanded configuration, which is at least about 1.5 times, and may be about 3 times, or as about 5 times, or as much as about 10 times, or even as much as about 15 times greater than a corresponding diameter of the device in a collapsed configuration. For instance, a 6 mm (length) stent may have a saddle diameter in a collapsed configuration of approximately 2.66 mm and in an expanded configuration of approximately 6 mm, with an expansion ratio of approximately 2.25; and a flange diameter in a collapsed configuration of approximately 2.66 mm and in an expanded configuration of approximately 14 mm, with an expansion ratio of approximately 5.26. A 20 mm (length) stent may have a saddle diameter in a collapsed configuration of approximately 3 mm and in an expanded configuration of approximately 20 mm, with an expansion ratio of approximately 6.66; and a flange diameter in a collapsed configuration of approximately 3 mm and in an expanded configuration of approximately 29 mm, with an expansion ratio of approximately 9.66. In devices with at least one lip along the retention members in accordance with various principles of the present disclosure, the lip length may be as short as about 1 mm and even as short as about 0.5 mm, and as long as about 1.5 mm, or as long as about 2.5 mm, or even as long as about 3 mm. In devices with at least one lip along the retention members in accordance with various principles of the present disclosure, the lip diameter may be at least about 1 mm wider or at least about 0.5 mm wider than the diameter of the saddle. In devices with at least one lip along the retention members in accordance with various principles of the present disclosure, the lip diameter may be as small as about 4 mm, or as small as about 6 mm, or as small as about 11 mm, and as large as about 22 mm, or as large as about 27 mm, including increments of 0.5 mm therebetween. For example, for a corresponding saddle diameter of about 10 mm, the lip diameter may be at least about 11 mm and at most about 14 mm; for a corresponding saddle diameter of about 15 mm, the lip diameter may be or at least about 16 mm and at most about 19 mm; and for a corresponding saddle diameter of about 20 mm, the lip diameter may be at least about 21 mm and at most about 24 mm, with all such dimensions including increments of 0.5 mm therebetween. In various embodiments of a stent with a lumen therethrough, the diameter of the lumen may be at least about 3 mm and at most about 60 mm, including diameters in increments of 0.5 mm therebetween. A device formed in accordance with various principles of the present disclosure may have a substantially constant diameter or a varying diameter along a longitudinal axis thereof. For example, a proximal end of a device formed in accordance with various principles of the present disclosure may have a proximal end with a smaller diameter than the diameter of the distal end, or larger diameters at the ends and a smaller diameter along the middle section. Various configurations and arrangements of sections which increase or decrease in diameter, or which have substantially constant diameters are within the scope and spirit of the present disclosure. Embodiments are not limited in this context.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A system for maintaining a flow path in tissue, comprising:
- a first sheath;
- a stent disposed within the first sheath, the stent configured to be deployed from the first sheath to transition between a first configuration, within the first sheath, and a second configuration, outside the first sheath;
- a second sheath disposed about the first sheath such that the first sheath extends longitudinally within the second sheath;
- a space defined between an exterior of the first sheath and an interior of the second sheath configured to retain a gel or liquid therein;
- a functional and/or therapeutic agent provided in a gel or liquid form or in a gel or liquid carrier and disposed within the space defined between the exterior of the first sheath and the interior of the second sheath and distally extrudable out of the space between the first sheath and the second sheath and onto the stent; and
- a cap provided along a distal end of the first sheath and/or a distal end of the second sheath and removable to allow release of the functional and/or therapeutic agent.

2. The system of claim 1, further comprising an inner member extending through the stent and having a cutting element disposed at a distal end thereof.

3. The system of claim 1, further comprising an inner member, wherein:
- the stent is disposed about an inner member; and
- the first sheath is proximally longitudinally retractable with respect to the inner member, the inner member is distally longitudinally extendable with respect to the first sheath, or both, such that the stent is released from within the first sheath to transition to the second configuration.

4. The system of claim 3, further comprising a cutting element disposed at an end of the inner member.

5. The system of claim 3, wherein the second sheath is proximally longitudinally retractable with respect to the inner member, the inner member is distally longitudinally extendable with respect to the second sheath, or both; and
- the system is configured to dispose the functional and/or therapeutic agent on the surface of the stent when the second sheath is proximally retracted with respect to the inner member, the inner member is distally extended with respect to the second sheath, or both.

6. The system of claim 1, wherein the system is configured to cause extrusion of the functional and/or therapeutic agent upon application of pressure into the space defined between the exterior of the first sheath and the interior of the second sheath.

7. The system of claim 1, wherein the functional and/or therapeutic agent comprises a first component, and a second component, the first component and the second component configured to react when in contact with each other.

8. The system of claim 7, wherein the first functional and/or therapeutic agent component is disposed between the first sheath and the second sheath, and the second functional and/or therapeutic agent component is disposed over the stent when disposed within the first sheath.

9. A system, comprising:
- a stent comprising a lumen extending longitudinally therethrough, the stent configured to shift between a first configuration and a second configuration;
- a functional and/or therapeutic agent delivered by the system in a gel or liquid form or in a gel or liquid carrier through a space surrounding yet not in communication with the stent when the stent is in the first configuration to be extruded over the stent when the stent is extended into the second configuration; and
- a cap provided along a distal end of the space surrounding the stent and removable to allow release of the functional and/or therapeutic agent;

wherein:
- in the second configuration, the stent defines a first retention member, a second retention member, and a saddle region extending therebetween; and
- when the stent is positioned within a body lumen in the second configuration, the first retention member, the second retention member, the saddle region, and the tissue wall of the lumen define a volume configured to retain the functional and/or therapeutic agent when extruded therein and over at least the saddle region.

10. The system of claim 9, wherein the first retention member and the second retention member are configured to space the tissue away from the saddle region.

11. The system of claim 9, wherein the functional and/or therapeutic agent comprises an agent selected from the group consisting of: an adhesive agent, a healing agent, a functional or therapeutic agent.

12. The system of claim 9, further comprising a fluid delivery device configured to inject the functional and/or therapeutic agent.

13. The system of claim 12, wherein the fluid delivery device is configured to inject the functional and/or therapeutic agent through the tissue wall and into the volume defined by the stent and the tissue wall.

14. The system of claim 9, further comprising a fluid delivery device configured to inject the functional and/or therapeutic agent, wherein the fluid delivery device is configured to extend through one of the first retention member or the second retention member to inject the functional and/or therapeutic agent into the volume defined by the stent and the tissue wall.

15. The system of claim 9, wherein the stent further comprises another functional and/or therapeutic agent disposed therealong.

16. A method for creating an anastomosis, including:

advancing a delivery system from a first lumen across first and second tissues and into a second lumen, wherein the delivery system comprises:

a first sheath;

an inner member;

a stent disposed within the first sheath and about the inner member, the stent configured to transition between a first configuration and a second configuration;

a second sheath disposed about the first sheath;

a functional and/or therapeutic agent in gel or liquid form, the functional and/or therapeutic agent disposed in a space defined between the first sheath and the second sheath; and a cap provided along a distal end of the first sheath and/or a distal end of the second sheath and removable to allow release of the functional and/or therapeutic agent;

removing the cap;

proximally retracting the first and second sheath with respect to the inner member, distally extending the inner member with respect to the first sheath and second sheath, or both such that:

a first end of the stent is extended distally outside the first sheath and forms the first retention member within the second body lumen; and the functional and/or therapeutic agent is disposed on a surface of the stent; and proximally retracting the first sheath with respect to the inner member, distally extending the inner member with respect to the first sheath, or both such that a second end of the stent is unconstrained from the first sheath and forms the second retention member within the first body lumen.

17. The method of claim 16, further comprising disposing the functional and/or therapeutic agent on at least one of the surface of the saddle region of the stent or the second retention member upon proximally retracting the first sheath with respect to the inner member, distally extending the inner member with respect to the first sheath, or both.

18. The method of claim 16, further comprising disposing an additional functional and/or therapeutic agent along a surface of the saddle region.

19. The method of claim 18, wherein disposing the additional functional and/or therapeutic agent comprises injecting the additional functional and/or therapeutic agent via a needle.

20. The method of claim 16, wherein the inner member comprises a cutting element disposed at an end thereof, and wherein the method further comprises forming an anastomosis across the first and second tissue with the cutting element before extending the first end of the stent distally outside the first sheath.

* * * * *